United States Patent
Kaddurah-Daouk

(10) Patent No.: US 6,288,124 B1
(45) Date of Patent: Sep. 11, 2001

(54) METHODS OF INHIBITING UNDESIRABLE CELL GROWTH USING AN AMINOGUANIDINE COMPOUND

(76) Inventor: Rima Kaddurah-Daouk, 4 Ross Rd., Belmont, MA (US) 02178

( * ) Notice: Subject to any disclaimer, the term of this patent is extended or adjusted under 35 U.S.C. 154(b) by 0 days.

(21) Appl. No.: 09/316,918

(22) Filed: May 21, 1999

Related U.S. Application Data

(60) Provisional application No. 60/086,585, filed on May 22, 1998, and provisional application No. 60/086,504, filed on May 22, 1998.

(51) Int. Cl.$^7$ .................................................. A60K 31/155
(52) U.S. Cl. .............................................................. 514/634
(58) Field of Search ............................................. 514/634

(56) References Cited

U.S. PATENT DOCUMENTS

| | | | |
|---|---|---|---|
| 3,412,105 | * 11/1968 | Langis ................................ | 260/340.5 |
| 5,449,688 | * 9/1995 | Wahl et al. ............................ | 514/546 |
| 5,676,978 | * 10/1997 | Teicher et al. ....................... | 424/649 |
| 5,994,577 | * 11/1999 | Larsen et al. ........................ | 560/168 |
| 6,093,745 | * 7/2000 | Hammes et al. ...................... | 514/634 |

FOREIGN PATENT DOCUMENTS

WO 96/16031    5/1996  (WO) .

OTHER PUBLICATIONS

Becker, S. et al., "Investigations on the function of creatine kinase in Ehrlich ascites tumor cells," *Biol. Chem. Hoppe Seyler*, 370(4):357–64 (1989), Feld, R.D. et al., "Presence of creatine kinase BB isoenzyme in some patients with prostatic carcinoma," *Clin. Chem.*, 23(10):1930–2 (1977).

Gazdar, A.F. et al., "Levels of creatine kinase and its BB isoenzyme in lung cancer specimens and cultures," *Cancer Res.*, 41(7):2773–7 (1981).

Homburger, H.A. et al., "Radioimmunoassay of creatine kinase B–isoenzymes in serum of patients with azotemia, obstructive uropathy, or carcinoma of the prostate or bladder," *Clin. Chem.*, 26(13):1821–4 (1980).

Ishiguro, Y. et al., "The diagnostic and prognostic value of pretreatment serum creatine kinase BB levels in patients with neuroblastoma," *Cancer*, 65(9):2014–9 (1990).

Kaddurrah–Daouk, R. et al., "Induction of a cellular enzyme for energy metabolism by transforming domains of adenovirus E1a," *Mol. Cell. Biol.*, 10(4):1476–83 (1990).

Lillie, J.W. et al., "Cyclocreatine (1–carboxymethyl–2–iminoimidazolidine) inhibits growth of a broad spectrum of cancer cells derived from solid tumors," *Cancer Res.*, 3(13):3172–8 (1993).

Ohira, Y. et al., "Reduced growth of Ehrlich ascites tumor cells in creatine depleted mice fed beta–guanidinopropionic acid," *Biochim. Biophys. Acta*, 1097(2):117–22 (1991).

Wallimann, T. et al., "Intracellular compartmentation, structure and function of creatine kinase isoenzymes in tissues with high and fluctuating energy demands: the 'phosphocreatine circuit' for cellular energy homeostasis," *Biochem. J.*, 281 (Pt 1):21–40 (1992).

* cited by examiner

Primary Examiner—Kevin E. Weddington
(74) Attorney, Agent, or Firm—Lahive & Cockfield, LLP; Elizabeth A. Hanley, Esq.

(57) ABSTRACT

The present invention provides for the use of aminoguanidines for prophylactic and/or therapeutic treatments of undesirable cell growth, e.g. tumors. The present invention provides methods of using aminoguanidines, optionally in combination with a hyperplastic inhibitory agent, to inhibit the growth of undesirable cells in a subject. The present invention is based, at least in part, on the discovery that aminoguanidines inhibit cell growth. The present invention further pertains to compositions for inhibiting undesirable cell growth in a subject. The compositions of the present invention include an effective amount of the aminoguanidine in a pharmaceutically acceptable carrier. Other aspects of the invention include a packaged aminoguanidine. The packaged compound includes instructions for using the aminoguanidine compound for inhibiting undesirable cell growth in a patient or instructions for using the compound in selected quantities, in a pharmaceutically acceptable carrier.

20 Claims, No Drawings

METHODS OF INHIBITING UNDESIRABLE CELL GROWTH USING AN AMINOGUANIDINE COMPOUND

RELATED APPLICATIONS

This application claims priority to U.S. Provisional Patent Application Ser. No. 60/086,585 filed on May 22, 1998, the entire contents of which are hereby expressly incorporated by reference. The entire contents of each of U.S. Ser. No. 07/610,418, filed Nov. 7, 1990, U.S. Ser. No. 07/467,147 filed Jan. 18, 1990, U.S. Ser. No. 07/344,963 filed Apr. 28, 1989, U.S. Ser. No. 07/310,773 filed Feb. 14, 1989, and U.S. Ser. No. 07/812,561 are hereby also expressly incorporated by reference. The entire contents of each of U.S. Provisional Patent Application Ser. No. 60/086,504 filed on May 22, 1998 and U.S. Patent Application Ser. No. (yet to be assigned) entitled "Use of Aminoguanidine or Aminoguanidine Analogs for the Treatment of Diseases of the Nervous System," filed on even date herewith, also are hereby expressly incorporated herein by reference.

BACKGROUND OF THE INVENTION

Worldwide, cancer is a leading cause of death. Presently, few cures exist for treating the various types of cancer. Among the possible cures that do exist include the application of tumor-inhibiting compounds (chemotherapy), radiation therapy, and bone-marrow transplants.

Transformation of cells results in changes in their growth characteristics and can cause them to form tumors in animals into whom they are introduced. For example, transformation of adherent cells can be associated with certain alterations such as changes in growth control, cell morphology, membrane characteristics, protein secretion and gene expression. Although transformation can occur spontaneously, it can be caused by a chemical or irradiation or may result from infection by a tumor virus. Little is known about the underlying molecular events. One type of RNA viruses (the retroviruses) and many different types of DNA viruses can act to transform cells and collectively are referred to as tumor viruses. In the case of tumor viruses, it is clear that the virus does not itself carry all of the genes necessary to produce the phenotypic changes characteristic of infected cells. Tumor viruses may act through a gene or genes in their genome (oncogenes) which, in some way, influence or induce target cell genes. The induced target cell genes, in turn, act to carry out the changes observed in transformed cells. There are at least three major classes of transforming DNA viruses: adenoviruses, which have two groups of oncogenes, ElA and ElB, which act together to produce transformation; papovaviruses, which synthesize proteins, called T antigens, which may work together to transform cells; and herpes viruses, for which no oncogene has been identified as yet.

Although considerable effort has been expended in identifying transforming genes or oncogenes and, in some cases, has also resulted in identification of their protein products, very little is known about the cellular mechanisms affected in the transformation process. There is a consensus that these oncogenes perturb cell growth by modifying the expression or activity of key growth related genes. It would be very helpful to have a better understanding of how transformation occurs, particularly if the biochemical pathways affected can be identified. Such knowledge would make it possible to design compounds which can interfere with or counter the effects of the transforming signals and, thus, are useful in preventing transformation or minimizing the extent to which it occurs, once begun, and, thus, to reduce effects on individuals in whom it occurs.

Prior art chemotherapy treatments typically include the application of chemotherapeutic agents to a patient in selected dosages to achieve and maintain a therapeutically effective level of the agents in the patient. However, most known chemotherapeutic agents used for the treatment of cancer display significant side effects. Thus, a drawback of typical chemotherapy treatments is that the compounds employed are non-specific in their activity and accumulate to toxic levels, and hence kill rapidly proliferating normal cells, as well as tumor cells.

Creatine Kinase (CK) is a purine metabolic enzyme that is intimately involved in the maintenance of ATP at various cites of cellular work. Typically, increased levels of CK are associated with cell transformation, and are thus used as markers to identify the same.

The creatine kinase (CK; EC 2.7.3.2) isozymes and their substrates, creatine and creatine phosphate (Cr-P), are believed to play a pivotal role in energy transduction in tissues with large fluctuating energy demands such as skeletal muscle heart and brain. The enzymes catalyze reversibly the transfer of the γ-phosphoryl group of ATP to creatine (Cr) to yield creatine phosphate (Cr-P) and ADP. The CK isozymes include three cytosolic forms, brain (CK-BB), muscle (CK-MM) and heart (CK-MB), as well as two mitochondrial forms, ubiquitous and sarcomeric.

A variety of important functions have been associated with the creatine kinase/creatine phosphate system (CK/CrP). Walliman et al., *Biochem. J.*, 281: 21–40 (1992). The Cr-P molecule seems to serve as an energy carrier connecting sites of energy production with sites of energy utilization via the subcellularly compartmentalized CK isoenzymes. A main function of the system is to provide appropriate local ATP/ADP ratios at subcellular sites where CK is functionally coupled to ATP consuming enzymes or processes. Another important function is to prevent increases in intracellular ADP levels during periods of cellular work, thus avoiding inactivation of cellular ATPases and net loss of adenine nucleotides.

It is now known that this enzyme system plays an important part in the metabolic events that take place during cell transformation. First, several studies of tumor cells have reported elevated levels of the brain isozyme of CK in several human tumors and in the serum of cancer patients. (see Ishiguro et al., *Cancer*, 65: 2014–2019 (1990); Gazdar et al., *Cancer Research*, 41: 2773–2777 (1981); Feld et al., *Clin. Chem.*, 23: 1930–1932 (1977); Homburger et al., *Clin. Chem.*, 26: 1821–1824 (1980); and Lillie et al., *Cancer Res.*, 53: 1–7 (1993). Second, the CK-BB gene is induced by the transforming domains of the adenovirus Ela oncogene (Kaddurah-Daouk et al., *Mol. Cell. Biol.*, 10: 1476–1483 (1990). Third, it has been noted that creatine is important for the growth of Ehrlich ascites tumors (Ohira et al., *Biochem. Biophys. Acta*, 1097: 117–122 (1991) and Becker S. and Schneider F., *Bio. Chem. Hoppe-Seyler*, 370: 357–365 (1989)).

SUMMARY OF THE INVENTION

The present invention is based, at least in part, on the discovery that aminoguanidine compounds inhibit undesirable cell growth, e.g. inappropriate cell growth resulting in undesirable benign conditions or tumor growth. The present invention provides for the use of aminoguanidine compounds for prophylactic and/or therapeutic treatments of undesirable cell growth. The present invention provides methods of using aminoguanidine compounds to inhibit the growth of undesirable cell growth in a subject. The present invention provides a method for inhibiting undesirable cell growth in a subject by administering to a subject an effective amount of aminoguanidine compound.

The present invention further pertains to compositions for inhibiting undesirable cell growth, e.g. tumor growth, in a subject. The copositions of the present invention include an effective amount of the aminoguanidine compound in a pharmaceutically acceptable carrier. Other aspects of the invention include packaged aminoguanidine compounds. The packaged compounds also include instructions for using the aminoguanidine compound for inhibiting undesirable cell growth in a patient or instructions for using the compound, in selected quantities, in a pharmaceutically acceptable carrier.

The methods and compositions of the present invention can be used for in vivo therapeutic purposes or can be used ex vivo for purging bone marrow. The bone marrow can be purged with the aminoguanidine compound and then placed back into the same subject or a different subject in its purged form. The methods and compositions of this invention also can be used in ex vivo screening assays for tissue or cells removed during surgery to determine whether the tissue or cells are cancerous or benign.

DETAILED DESCRIPTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention pertains to a method of inhibiting undesirable cell growth in a subject. The method involves the administration of an effective amount of an aminoguanidine compound to the subject such that growth of the undesirable cell(s) is inhibited.

The term "administering" is intended to include routes of administration which allow the aminoguanidine compound to perform its intended function of inhibiting undesirable cell growth. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the aminoguanidine compound or inhibitory agent can be coated with or disposed in a selected material to protect it from natural conditions which may detrimentally effect its ability to perform its intended function. The aminoguanidine compound can be administered alone, or in conjunction with either an inhibitory agent or with a pharmaceutically acceptable carrier, or both. Further the aminoguanidine compound can be administered as a mixture of aminoguanidine compounds, which also can be coadministered with at least one inhibitory agent, or pharmaceutically acceptable carrier, or both. The aminoguanidine compound can be administered prior to the administration of the inhibitory agent, simultaneously with the inhibitory agent, or after the administration of the inhibitory agent. The aminoguanidine compound also can be administered as a prodrug which is converted to its active form in vivo.

Compounds which are particularly effective for this purpose include aminoguanidine, aminoguanidines, diaminoguanidine, diaminoguanidines and analogs thereof which are described in detail below. The term "aminoguanidine compounds" will be used herein to include aminoguanidines and diaminoguanidines, such as aminoguanidine phosphate, and compounds which are structurally similar to aminoguanidine or aminoguanidine phosphate, and analogs of aminoguanidine and aminoguanidine phosphate.

The term "aminoguanidine compounds" also includes compounds which "mimic" the activity of aminoguanidine and diaminoguanidine, such as aminoguanidine, aminoguanidine phosphate or aminoguanidine analogs, i.e., compounds which inhibit or modulate the creatine kinase system. The term "aminoguanidine" is intended not to include guanidine. The term "mimics" is intended to include compounds which may not be structurally similar to aminoguanidine or diaminoguanidine but mimic the therapeutic activity of these compounds, such as aminoguanidine, aminoguanidine phosphate or structurally similar compounds. The term "inhibitors of creatine kinase system" are compounds which inhibit the activity of the creatine kinase enzyme, molecules that inhibit the creatine transporter or molecules that inhibit the binding of the enzyme to other structural proteins or enzymes or lipids.

The term "modulators of the creatine kinase system" are compounds which modulate the activity of the enzyme, or the activity of the transporter of creatine or the ability of other proteins or enzymes or lipids to interact with the system. The term "aminoguanidine analog" is intended to include compounds which are structurally similar to aminoguanidine or diaminoguanidine compounds such as aminoguanidine phosphate compounds which are art recognized as being analogs of aminoguanidine or aminoguanidine phosphate, and/or compounds which share the same or similar function as aminoguanidine or aminoguanidine phosphate.

The language "pharmaceutically acceptable carrier" is intended to include substances capable of being coadministered with the aminoguanidine compound(s) and/or the inhibitory agent(s), and which allows both to perform their intended function of inhibiting undesirable cell growth in a subject. Examples of such carriers include solutions, solvents, dispersion media, delay agents, emulsions and the like. The use of such media for pharmaceutically active substances are well known in the art. Any other conventional carrier suitable for use with the aminoguanidine compound and/or with the inhibitory agent(s) also fall within the scope of the present invention.

The language "effective amount" of the aminoguanidine compound is that amount necessary or sufficient to inhibit the undesirable cell growth, e.g. prevent the undesirable cell growth, or reduce the size of a pre-existing benign cell mass or malignant tumor in the subject. The effective amount can vary depending on such factors as the type of cell growth being treated or inhibited. the type of inhibitory agent(s) employed, the particular creatine compound, the size of the subject, or the severity of the undesirable cell growth or tumor. For example, the choice of each of the agent (aminoguanidine compound) can affect what constitutes an "effective amount". One of ordinary skill in the art would be able to study the aforementioned factors and make the determination regarding the effective amount of the aminoguanidine compound and inhibitory agent, if present, without undue experimentation. An in vitro assay can be used to determine an "effective amount" of the aminoguanidine compound. The ordinarily skilled artisan would select an appropriate amount of the agent for use in the aforementioned in vitro assay. The cell survival fraction can be used to determine whether the selected amount was an "effective amount". For example, the selected amount used within the assay preferably should result in a killing of at least 50% of the cells, more preferably 75%, and most preferably at least 95%.

The regimen of administration also can affect what constitutes an effective amount. The aminoguanidine compound can be administered to the subject prior to, simultaneously with, or after the administration of other inhibitory agent(s). Further, several divided dosages, as well as staggered dosages, can be administered daily or sequentially, or the dose can be continuously infused. Further, the dosages of the compound and the agent(s) can be proportionally increased or decreased as indicated by the exigencies of the therapeutic situation.

Aminoguanidine compounds of this invention are those encompassed by the general formula I

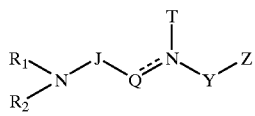

wherein
a) $R_1$ through $R_{16}$, if present, are selected from the group consisting of hydrogen, alkyl, alkenyl, alkynyl, and alkoxyl;
b) J is either

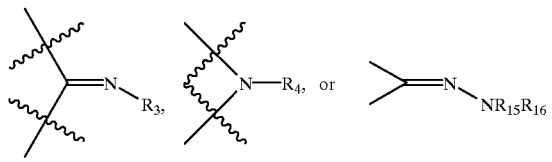

c) Q is either

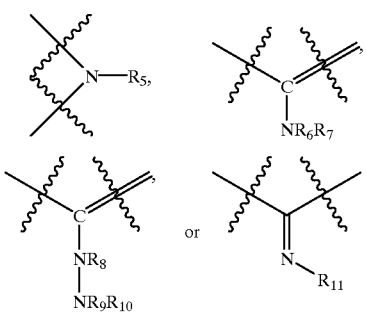

d) T, if present, is $R_{12}$ or $NR_{13}R_{14}$;
e) Y is an alkylene, alkenylene, alkynylene or an alkoxylene;
f) Z is selected from the group consisting of

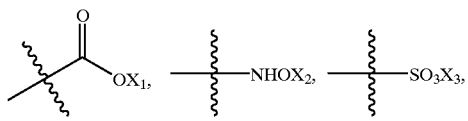

-continued

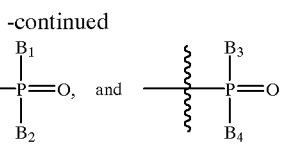

wherein $B_1$–$B_4$ are each independently selected from hydrogen and $OX_4$ and $X_1$–$X_4$ are each independently selected from the group consisting of hydrogen, alkyl, alkenyl, alkynyl and pharmaceutically acceptable salts; and wherein Y and Q or N and Q can form a ring structure.

The alkylene, alkenylene, alkynylene, alkyl, alkenyl and alkynyl groups (hereinafter hydrocarbon groups) may have straight or branched chains. The unsaturated groups may have a single site of unsaturation or a plurality of sites of unsaturation. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, methylene, ethyl, ethylene, ethenyl, ethenylene, ethynl, ethynylene, propyl, propylene, propenyl, propenylene, propynyl, and propynylene. Examples of higher hydrocarbon groups (from four to about ten carbons) include butyl, t-butyl, butenyl, butenylene, and butynyl, butynylene, nonyl, nonylene, nonenyl, nonenylene, nonynyl, and nonynylene.

The alkoxy, haloalkyl, alkoxyene, and haloalkylene groups (hereinafter substituted hydrocarbon groups) are alkyl or alkylene groups substituted with one or more oxygen or halogen atoms. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, and iodine. Examples of substituted hydrocarbon groups which are useful within this invention are similar to hydrocarbon groups set forth above except for the incorporation of oxygen(s) or halogen(s) into the groups.

The language "pharmaceutically acceptable salt" (as a possibility for "X" in formula (I) and as it pertains to aminoguanidine compound salts) is intended to include pharmaceutically acceptable salts capable of being solvated under physiological conditions. Examples of such salts include sodium, e.g. disodium, potassium, e.g. dipotassium, and hemisulfate. The term is further intended to include lower hydrocarbon groups capable of being solvated under physiological conditions, i.e. alkyl esters, e.g. methyl, ethyl and propyl esters.

The nitrogen of formula I and Q or Q and Y can form a ring. The ring can be a hydrocarbon ring or a hetero ring containing atoms such as O, N or S. The ring structure further can be a single ring or alternatively can be a fused ring system. The preferred ring structures are single rings having five, six or seven ring members and most preferably five membered rings such as those present in cycloaminoguanidine- or carboaminoguanidine-like compounds, e.g.,

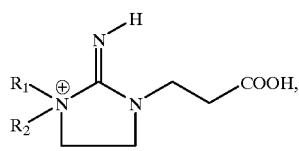

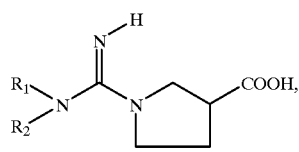

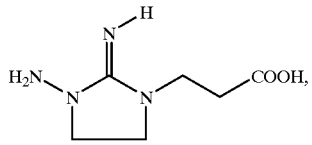

or

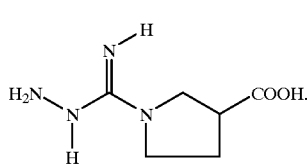

In one aspect of the invention, aminoguanidine compounds include

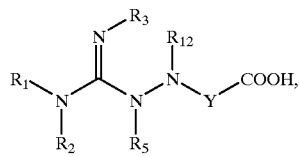

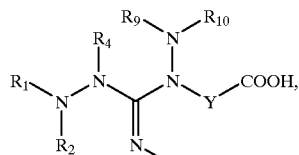

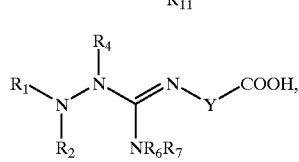

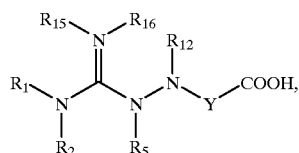

and

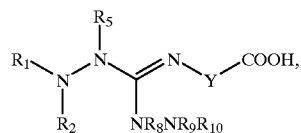

wherein $R_1$–$R_{16}$ and Y are as defined above. Optionally $R_2$ and $R_5$ or $R_2$ and $R_6$ or $R_2$ and $R_8$, together, can form a ring.

In another aspect of the invention, aminoguanidine compounds include

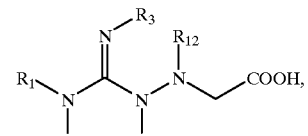

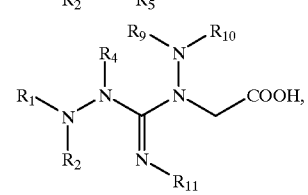

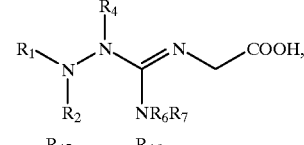

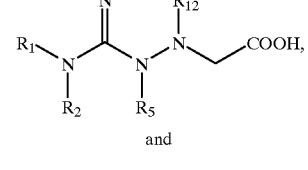

and

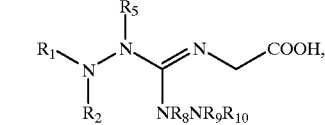

wherein $R_1$–$R_{16}$ are as described above. Optionally $R_2$ and $R_5$ or $R_2$ and $R_6$ or $R_2$ and $R_8$, together, can form a ring.

Preferred aminoguanidine compounds of the invention are

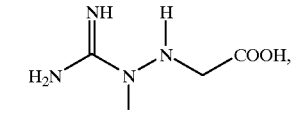

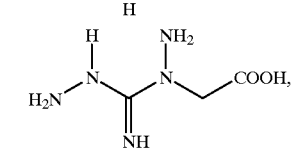

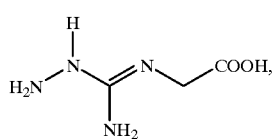

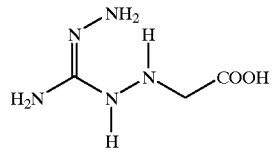

and

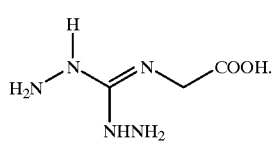

Aminoguanidine, aminoguanidine phosphate and many aminoguanidine analogs, and competitive inhibitors are commercially available and/or have been previously synthesized and are known in the literature.

Synthesis of guanidinoalkylcarboxylic acids can be accomplished by condensation of substituted or unsubstituted amino acid with a substituted or unsubstituted cyanamide. For example, 3-guanidinopropionic acid is commercially available and can be prepared as follows:

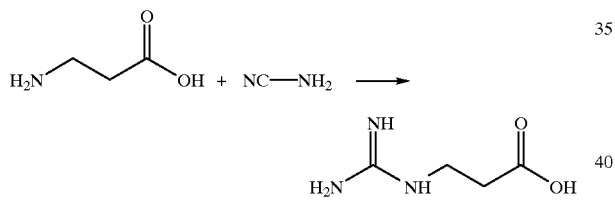

Preparation of [1-(hydrazinoiminomethyl)hydrazino]-acetic acids of the invention can be accomplished by the following synthetic procedure:

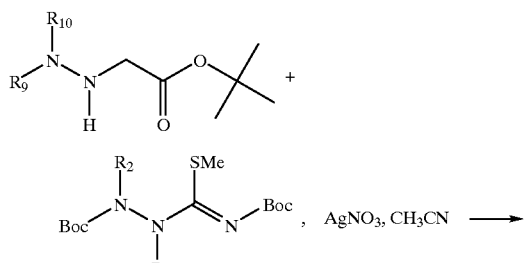

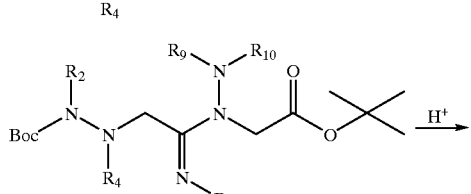

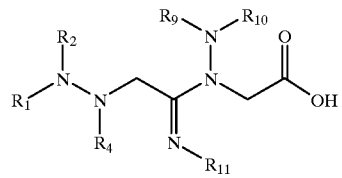

wherein $R_1$–$R_{11}$ are as defined above. For example, preparation of (CAS # 179474-69-2) can be accomplished by the following synthetic procedure:

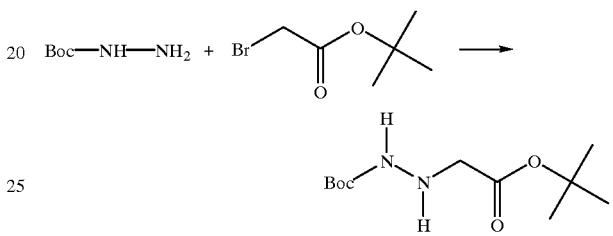

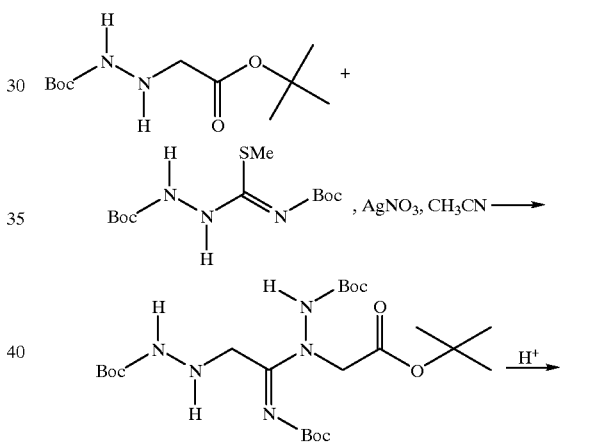

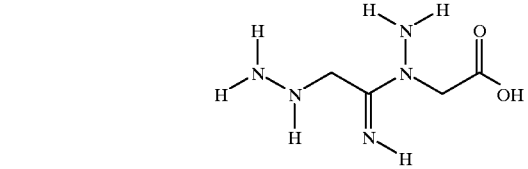

wherein preparation of

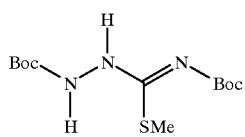

can be accomplished by the following reactions sequence:

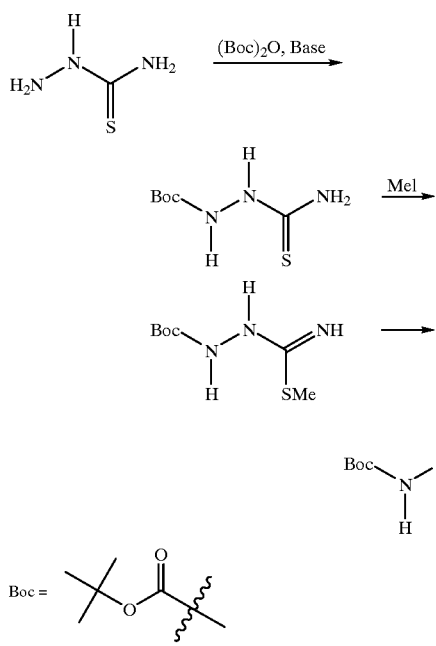

[2-(aminoiminomethyl)hydrazino]-acetic acids of the invention can be prepared known synthetic procedures. For example preparation of (CAS # 179474-55-6) can be accomplished by the following synthetic procedure:

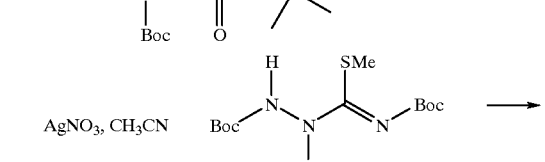

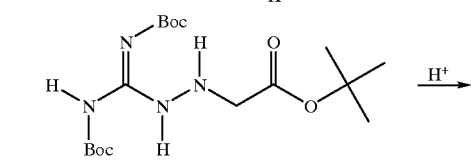

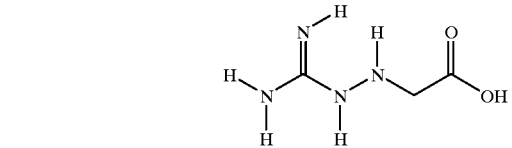

[2-(hydrazinoiminomethyl)hydrazino]-acetic acids of the invention can be prepared known synthetic procedures. For example preparation of (CAS # 179474-62-5) can be accomplished by the following synthetic procedure:

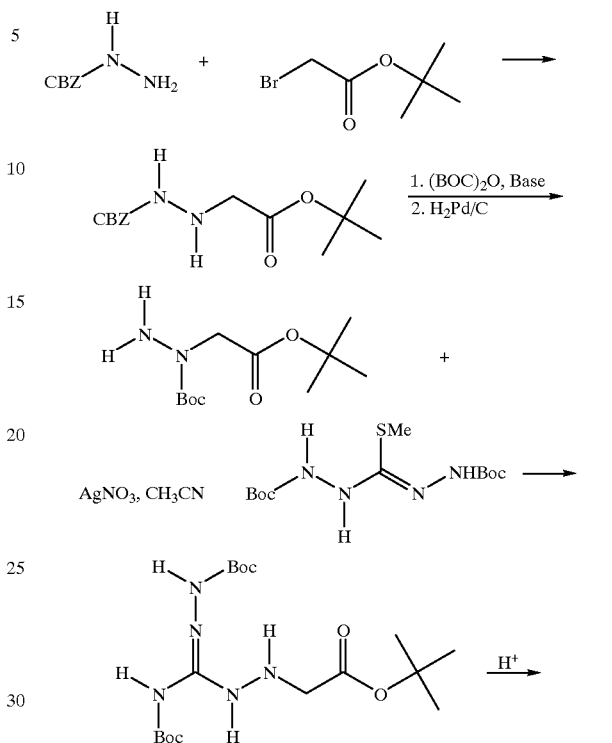

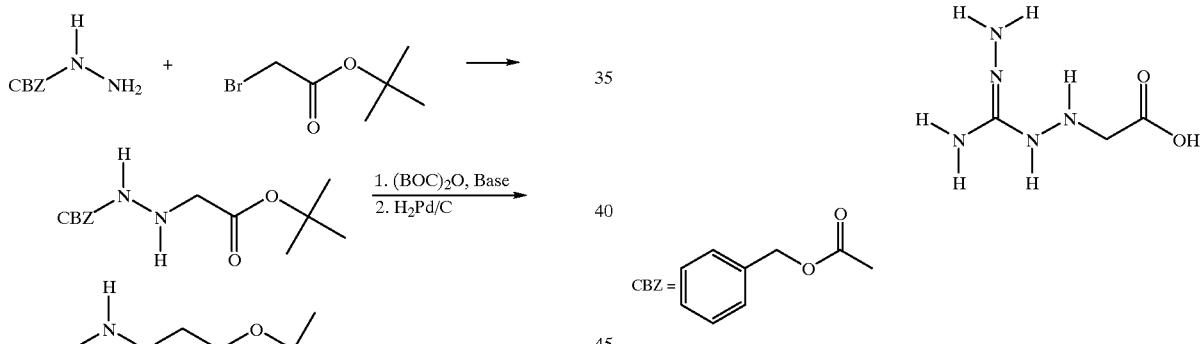

N-(hydrazinoiminomethyl)-glycines of the invention can be prepared known synthetic procedures. For example preparation of (CAS # 17901-84-7) can be accomplished by the following synthetic procedure:

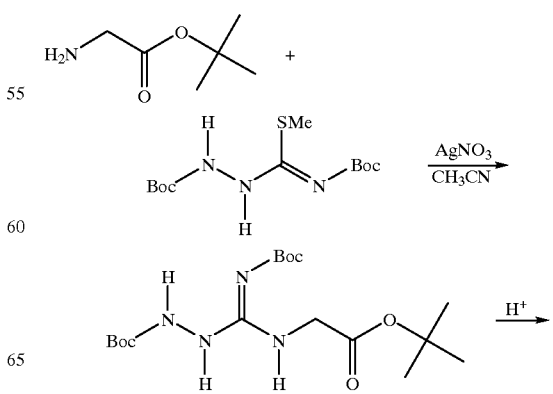

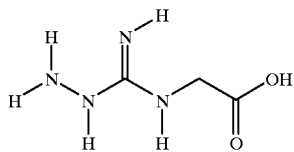

N-(hydrazinohydrazinomethyl)-glycines of the invention can be prepared known synthetic procedures. For example preparation of (CAS # 179474-61-4) can be accomplished by the following synthetic procedure:

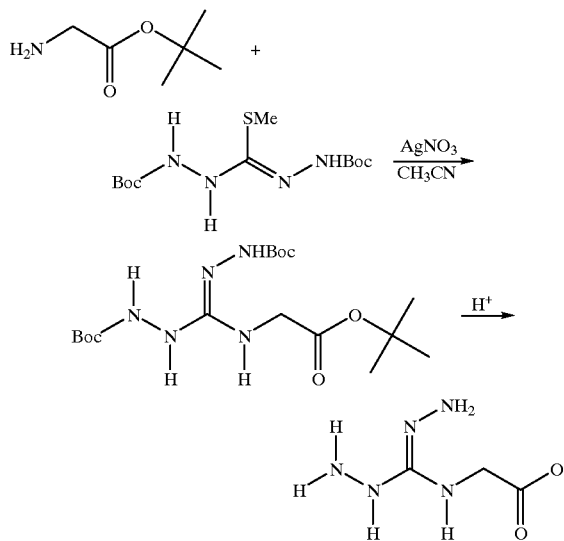

wherein preparation of

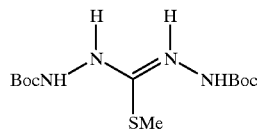

can be accomplished by the following sequence:

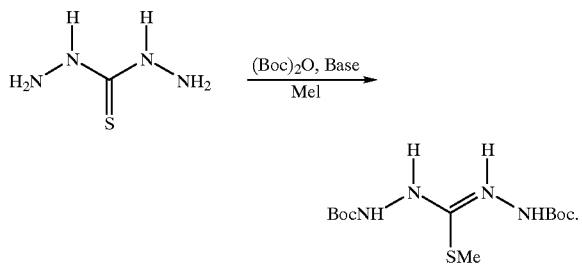

Additionally, analogs of aminoguanidine may be synthesized using conventional techniques (See for example Larson, Scott D. et al. PCT Int. Appl. WO 96 16,031, the contents of which are hereby expressly incorporated by reference). For example, aminoguanidine can be used as the starting material for synthesizing at least some of the analogs encompassed by formula I. Appropriate synthesis reagents, e.g. alkylating, alkenylating or alkynylating agents may be used to attach the respective groups to target sites. Alternatively, reagents capable of inserting spacer groups may be used to alter the aminoguanidine structure. Sites other than the target site are protected using conventional protecting groups while the desired sites are being targeted by synthetic reagents.

Some specific examples of aminoguanidine compounds of the present invention include cycloaminoguanidine, cycloaminoguanidine phosphate, aminoguanidine, aminoguanidine phosphate (phosphoaminoguanidine), homocycloguanidine and homocycloguanidine phosphate. Cycloaminoguanidine is an essentially planar cyclic analog of aminoguanidine. Although cycloaminoguanidine is structurally similar to aminoguanidine, the two compounds are believed to be distinguishable both kinetically and thermodynamically.

The phosphorylated compound P-cycloaminoguanidine is structurally similar to phosphoaminoguanidine; however, the phosphorous-nitrogen (P—N) bond of cycloaminoguanidine phosphate is believed to be more stable than that of phosphoaminoguanidine. Aminoguanidine compounds which can act as substrates for creatine kinase are at least some of the compounds which are intended to be part of this invention. Examples of such aminoguanidine and diaminoguanidine compounds are included in Table 1.

TABLE 1

Aminoguanidine Analogs

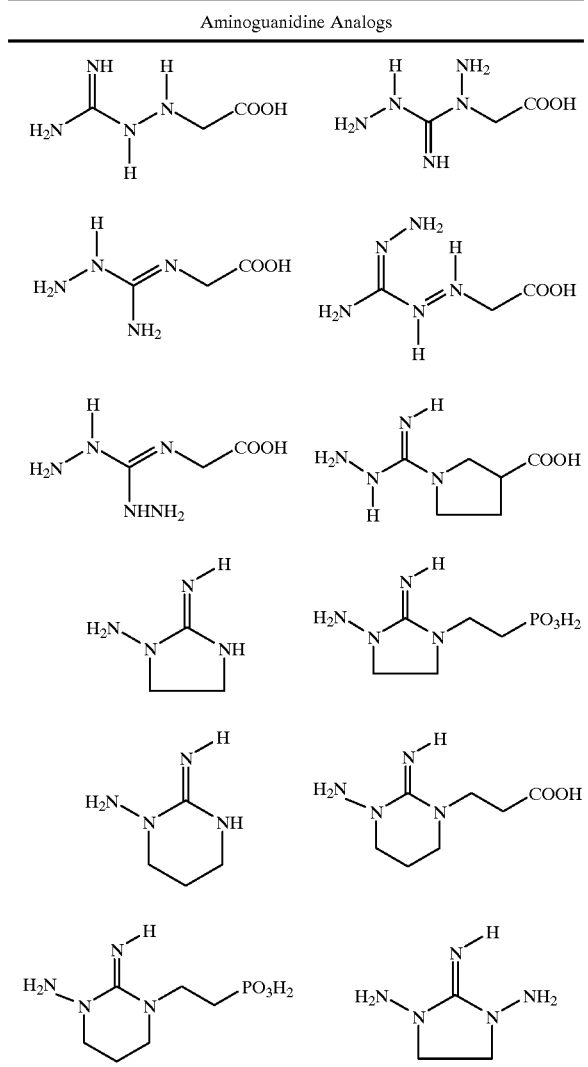

TABLE 1-continued

Aminoguanidine Analogs

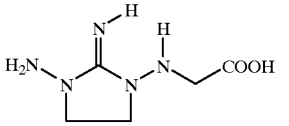
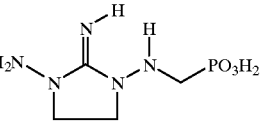
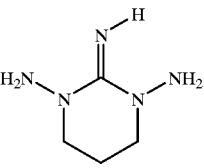
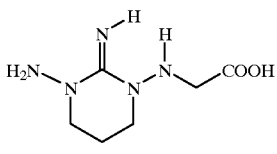
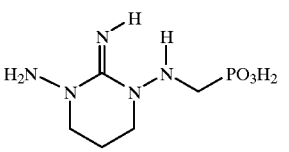

Salts of the products may be exchanged to other salts using standard protocols. The enzymatic synthesis utilizes the creatine kinase enzyme, which is commercially available, to phosphorylate the aminoguanidine compounds. ATP is required by creatine kinase for phosphorylation, hence it needs to be continuously replenished to drive the reaction forward. It is necessary to couple the creatine kinase reaction to another reaction that generates ATP to drive it forward. The purity of the resulting compounds can be confirmed using known analytical techniques including $^1$H NMR, $^{13}$C NMR Spectra, Thin layer chromatography, HPLC and elemental analysis.

The aminoguanidine compounds of this invention preferably possess inherent characteristics enhancing their ability to perform their intended function of inhibiting tumor growth. For example, the aminoguanidine compounds preferably have a solubility which allows them to be delivered in vivo and/or are capable of acting as substrates for aminoguanidine kinase. Some examples of aminoguanidine compounds of the present invention are set forth below in Table 1.

The term "subject" is intended to include mammals having undesirable cell growth, e.g. tumors, or which are susceptible to undesirable cell growth, e.g. tumors. Examples of such subjects include humans, dogs, cats, pigs, cows, horses, rats, and mice.

The language "hyperplastic inhibitory agent" is intended to include agents that inhibit the growth of proliferating cells or tissue wherein the growth of such cells or tissues is undesirable. For example, the inhibition can be of the growth of malignant cells such as in neoplasms or benign cells such as in tissues where the growth is inappropriate. Examples of the types of agents which can be used include chemotherapeutic agents, radiation therapy treatments and associated radioactive compounds and methods, and immunotoxins.

The language "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics*, 8th Ed., Sec 12:1202-1263 (1990)), and are typically used to treat neoplastic diseases. The chemotherapeutic agents generally employed in chemotherapy treatments are listed below in Table 2.

TABLE 2

| CLASS | TYPE OF AGENT | NONPROPRIETARY NAMES (OTHER NAMES) |
|---|---|---|
| Alkylating | Nitrogen Mustards | Mechlorethamine (HN$_2$) |
| | | Cyclophosphamide |
| | | Ifosfamide |
| | | Melphalan (L-sarcolysin) |
| | | Chlorambucil |
| | Ethylenimines and Methylmelamines | Hexamethylmelamine Thiotepa |
| | Alkyl Sulfonates | Busulfan |
| | Nitrosoureas | Carmustine (BCNU) |
| | | Lomustine (CCNU) |
| | | Semustine (methyl-CCNU) |
| | | Streptozocin (streptozotocin) |
| | Triazenes | Decarbazine (DTIC; dimethyltriazenoimi-dazolecarboxamide) |
| | Alkylator | cis-diamminedichloroplatinum II (CDDP) |
| Antimeta-bolites | Folic Acid Analogs | Methotrexate (amethopterin) |
| | Pyrimidine Analogs | Fluorouracil ('5-fluorouracil; 5-FU) |
| | | Floxuridine (fluorode-oxyuridine; FUdR) |
| | | Cytarabine (cytosine arabinoside) |
| | Purine Analogs and Related Inhibitors | Mercaptopuine (6-mercaptopurine; 6-MP) |
| | | Thioguanine (6-thioguanine; TG) |
| | | Pentostatin (2' - deoxycoformycin) |
| Natural Products | Vinca Alkaloids | Vinblastin (VLB) |
| | | Vincristine |
| | Topoisomerase Inhibitors | Etoposide |
| | | Teniposide |
| | | Camptothecin |
| | | Topotecan |
| | | 9-amino-campotothecin CPT-11 |
| | Antibiotics | Dactinomycin (actinomycin D) |
| | | Adriamycin |
| | | Daunorubicin (daunomycin; rubindomycin) |
| | | Doxorubicin |
| | | Bleomycin |
| | | Plicamycin (mithramycin) |
| | | Mitomycin (mitomycin C) |
| | | Taxol |
| | | Taxotere |
| | Enzymes | L-Asparaginase |
| | Biological Response Modifiers | Interfon alfa interleukin 2 |
| Miscell-aneous Agents | Platinum Coordination Complexes | cis-diamminedichloroplatinum II (CDDP) Carboplatin |
| | Anthracendione | Mitoxantrone |
| | Substituted Urea | Hydroxyurea |
| | Methyl Hydraxzine Derivative | Procarbazine (N-methylhydrazine, MIH) |
| | Adrenocortical Suppressant | Mitotane (o,p'-DDD) Aminoglutethimide |
| Hormones and Anta- | Adrenocorticosteriods Progestins | Prednisone Hydroxyprogesterone caproate |

TABLE 2-continued

| CLASS | TYPE OF AGENT | NONPROPRIETARY NAMES (OTHER NAMES) |
|---|---|---|
| gonists | | Medroxyprogesterone acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| | Antiandrogen | Flutamide |
| | Gonadotropin-releasing hormone analog | Leuprolidel |

The language "radiation therapy" is intended to include the application of a genetically and somatically safe level of x-rays, both localized and non-localized, to a subject to inhibit, reduce, or prevent symptoms or conditions associated with undesirable cell growth. The term x-rays is intended to include clinically acceptable radioactive elements and isotopes thereof, as well as the radioactive emissions therefrom. Examples of the types of emissions include alpha rays, beta rays including hard betas, high energy electrons, and gamma rays. Radiation therapy is well known in the art (see e.g., Fishbach, F., *Laboratory Diagnostic Tests,* 3rd Ed., Ch. 10: 581–644 (1988)), and is typically used to treat neoplastic diseases.

The term "immunotoxins" includes immunotherapeutic agents which employ cytotoxic T cells and/or antibodies, e.g., monoclonal, polyclonal, phage antibodies, or fragments thereof, which are utilized in the selective destruction of undesirable rapidly proliferating cells. For example, immunotoxins can include antibody-toxin conjugates (e.g., Ab-ricin and Ab-diptheria toxin), antibody-radiolabels (e.g., Ab-$I^{135}$) and antibody activation of the complement at the tumor cell. The use of immunotoxins to inhibit, reduce, or prevent symptoms or conditions associated with neoplastic diseases are well known in the art (see e.g., Harlow, E. and Lane, D., *Antibodies,* (1988)).

The language "inhibiting undesirable cell growth" is intended to include the inhibition of undesirable or inappropriate cell growth. The inhibition is intended to include inhibition of proliferation including rapid proliferation. For example, the cell growth can result in benign masses or the inhibition of cell growth resulting in malignant tumors. Examples of benign conditions which result from inappropriate cell growth or angiogenesis are diabetic retinopathy, retrolental fibroplasia, neovascular glaucoma, psoriasis, angiofibromas, rheumatoid arthritis, hemangiomas, Karposi's sarcoma, and other conditions or dysfunctions characterized by dysregulated endothelial cell division.

The language "inhibiting tumor growth" is intended to include the prevention of the growth of a tumor in a subject or a reduction in the growth of a pre-existing tumor in a subject. The inhibition also can be the inhibition of the metastasis of a tumor from one site to another. In particular, the language "tumor" is intended to encompass both in vitro and in vivo tumors that form in any organ or body part of the subject. The tumors preferably are tumors sensitive to the aminoguanidine compounds of the present invention. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys. Specifically, the tumors whose growth rate is inhibited by the present invention include basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

The present invention further pertains to a therapeutic and prophylactic composition for inhibiting tumor growth in a subject. The composition contains an effective amount of an aminoguanidine compound and a pharmaceutically acceptable carrier.

The present invention further pertains to packaged tumor growth inhibitors containing an aminoguanidine compound packaged with instructions for using the aminoguanidine compound as a tumor growth inhibitor. The instructions would provide such information as the appropriate dose of aminoguanidine or the appropriate regimen.

The contents of all references, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method for inhibiting undesirable cell growth in a subject, comprising administering to a subject an effective amount of an aminoguanidine such that the undesirable cell growth is inhibited.

2. The method of claim 1, wherein the undesirable cell growth is inappropriate cell growth.

3. The method of claim 2, wherein the inappropriate cell growth results in a condition selected from the group consisting of diabetic retinopathy, retrolental fibroplasia, neovascular glaucoma, angiofibromas, hemangiomas, and Karposi's sarcoma.

4. The method of claim 1, wherein the inhibition of undesirable cell growth is the inhibition of tumor growth.

5. The method of claim 4, wherein tumor growth is inhibited by preventing the occurrence of the tumor in the subject.

6. The method of claim 4, wherein tumor growth is inhibited by reducing the growth of a pre-existing tumor.

7. The method of claim 1, wherein said aminoguanidine has the general formula I

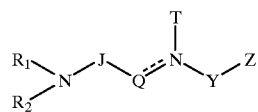

wherein a) $R_1$ through $R_{16}$, if present, are selected from the group consisting of hydrogen, alkyl, alkenyl, alkynyl, and alkoxyl;

b) J is either

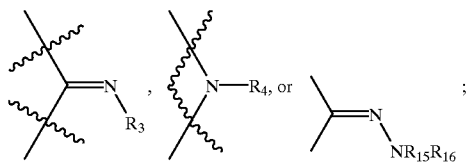

c) Q is either

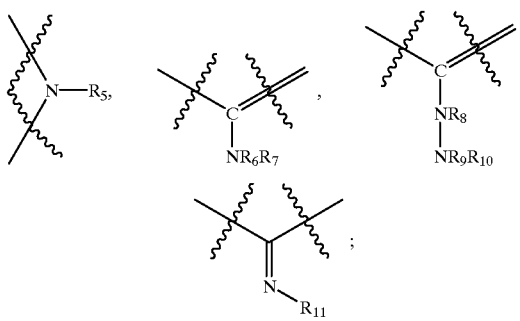

d) T, if present, is $R_{12}$ or $NR_{13}R_{14}$;

e) Y is an alkylene, alkenylene, alkynylene or an alkoxylene;

f) Z is selected from the group consisting of

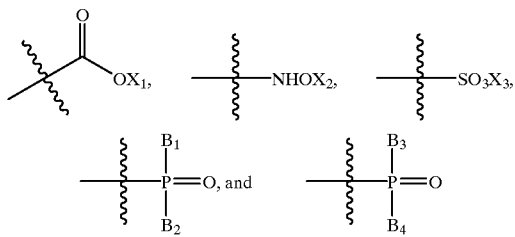

wherein $B_1$–$B_4$ are each independently selected from hydrogen and $OX_4$ and $X_1$–$X_4$ are each independently selected from the group consisting of hydrogen, alkyl, alkenyl, alkynyl and pharmaceutically acceptable salts; and wherein Y and Q or N and Q can form a ring structure.

8. The method of claim 1, wherein said aminoguanidine is selected from the group consisting of:

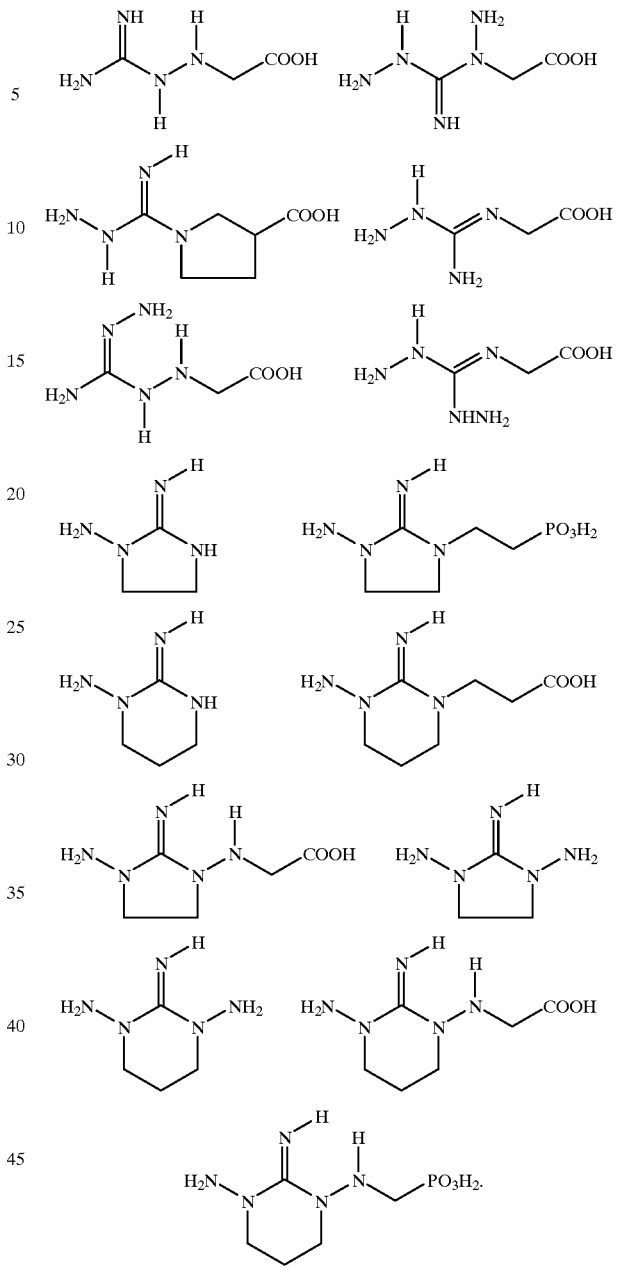

9. The method of claim 1, further comprising a hyperplastic inhibitory agent.

10. The method of claim 9, wherein said hyperplastic inhibitory agent is cis-diammine dichloroplatinum (II).

11. The method of claim 9, wherein said hyperplastic inhibitory agent is an alkylating agent.

12. The method of claim 11, wherein said alkylating agent is selected from the group consisting of nitrogen mustards, ethylenimines, methylmelamines, alkyl sulfonates, nitrosoureas, and triazenes.

13. A composition for inhibiting undesirable cell growth in a subject, comprising
an effective amount of an aminoguanidine, and
a pharmaceutically acceptable carrier, wherein said aminoguanidine is of formula I:

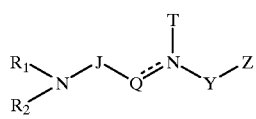

wherein
a) $R_1$ through $R_{16}$, if present, are selected from the group consisting of hydrogen, alkyl, alkenyl, alkynyl, and alkoxyl;
b) J is either

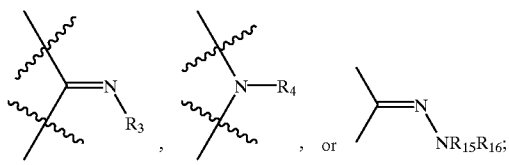

c) Q is either

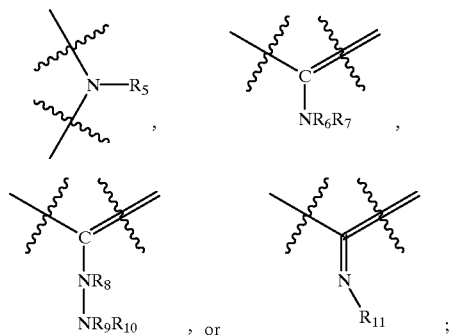

d) T, if present, is $R_{12}$ or $NR_{13}R_{14}$;
e) Y is an alkylene, alkenylene, alkynylene or an alkoxylene;
f) Z is selected from the group consisting of

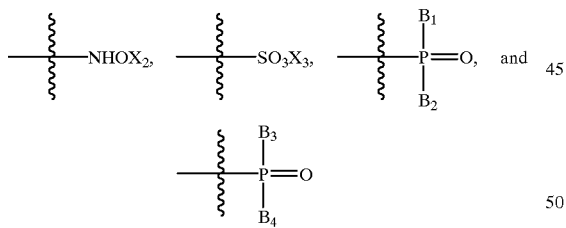

wherein $B_1$–$B_4$ are each independently selected from hydrogen and $OX_4$ and $X_1$–$X_4$ are each independently selected from the group consisting of hydrogen, alkyl, alkenyl, alkynyl and pharmaceutically acceptable salts; and
wherein Y and Q or N and Q can form a ring structure.

14. A composition for inhibiting undesirable cell growth in a subject, comprising
an effective amount of an aminoguanidine,
a pharmaceutically acceptable carrier and a hyperplastic inhibitory agent.

15. The composition of claim 14, wherein said hyperplastic inhibitory agent is cis-diammine dichloroplatinum (II).

16. The composition of claim 14, wherein said hyperplastic inhibitory agent is an alkylating agent.

17. The composition of claim 16, wherein said alkylating agent is selected from the group consisting of nitrogen mustards, ethylenimines, methylmelamines, alkyl sulfonates, nitrosoureas, and triazenes.

18. A packaged undesirable cell growth inhibitor, comprising
an aminoguanidine packaged with instructions for using an effective amount of said aminoguanidine as an undesirable cell growth inhibitor to treat diabetic retinopathy, retrolental fibrioplasia, neovascular glaucoma, angiofibromas, hemangiomas, or Karposi's sarcoma.

19. The packaged undersirable cell growth inhibitor of claim 18, wherein said aminoguanidine has the general formula I

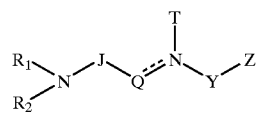

wherein
a) $R_1$ through $R_{16}$, if present, are selected from the group consising of hydrogen, alkyl, alkenyl, alkynyl, and alkoxyl;
b) J is either

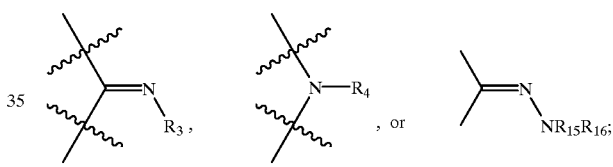

c) Q is either

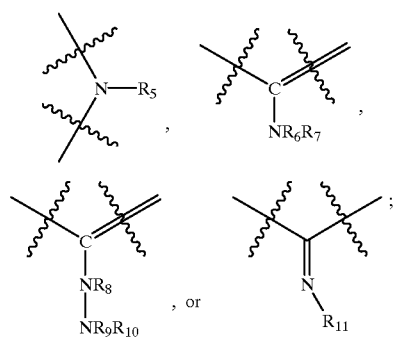

d) T, if present, is $R_{12}$ or $NR_{13}R_{14}$;
e) Y is an alkylene, alkenylene, alkynylene of an alkoxylene;
f) Z is selected from the group consisting of

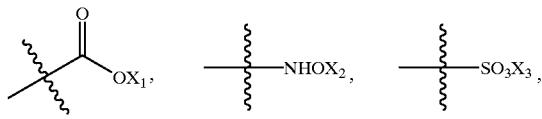

-continued

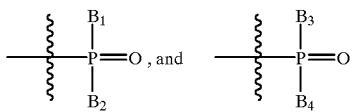

wherein $B_1$–$B_4$ are each independently selected from hydrogen and $OX_4$ and $X_1$–$X_4$ are each independently selected from the group consisting of hydro-gen alkyl, alkenyl, alkynyl and pharmaceutically acceptable salts; and where in Y and Q or N and Q can form a ring structure.

20. A method for preventing tumor growth in a subject, comprising administering to a subject an effective amount of an aminoguanidine such that tumor growth is prevented.

* * * * *